United States Patent [19]
Baudino et al.

[11] Patent Number: 5,458,629
[45] Date of Patent: Oct. 17, 1995

[54] IMPLANTABLE LEAD RING ELECTRODE AND METHOD OF MAKING

[75] Inventors: Michael D. Baudino, Coon Rapids; Brian T. Stolz, Bloomington; Mark A. Taube, Andover, all of Minn.

[73] Assignee: Medtronic, Inc., Minneapolis, Minn.

[21] Appl. No.: 198,933

[22] Filed: Feb. 18, 1994

[51] Int. Cl.[6] ........................................... A61N 1/04
[52] U.S. Cl. ............................. 607/116; 128/642
[58] Field of Search ............... 128/642; 607/115, 607/116, 119, 122–128

[56] References Cited

U.S. PATENT DOCUMENTS

| | | | |
|---|---|---|---|
| 3,995,623 | 12/1976 | Blake et al. | 128/2.06 E |
| 4,280,511 | 7/1981 | O'Neill | 128/784 |
| 4,379,462 | 4/1983 | Borkan et al. | 128/786 |
| 4,432,377 | 2/1984 | Dickhudt | 128/786 |
| 4,437,474 | 3/1984 | Peers-Trevarton | 128/784 |
| 4,458,695 | 7/1984 | Peers-Trevarton | 128/786 |
| 4,592,372 | 6/1986 | Beranek | 128/786 |
| 4,608,986 | 9/1986 | Beranek et al. | 128/786 |
| 5,246,016 | 9/1993 | Lieber et al. | 128/898 |

OTHER PUBLICATIONS

"Pisces Quad© For Spinal Cord Stimulation (SCS) Model 3487A Lead," *Medtronic Lead Implant Manual*, Medtronic, Inc., Copyright 1990.

*Primary Examiner*—William E. Kamm
*Attorney, Agent, or Firm*—Curtis D. Kinghorn; Harold R. Patton

[57] ABSTRACT

A novel flexible and highly fatigue resistant neural lead is provided having a body with multiple lumens, one of which may receive a stiffening stylet, and the others of which serve as conduits for bundle stranded wire conductors which make contact with ring electrodes at the distal end of the lead. The ring electrodes will be constructed according to a novel technique in which the body of the lead is etched or milled to provide notches and the ring electrodes are formed by enplacing a C-shaped conductor over the notch and closing it into place to provide an isodiametric lead construction.

18 Claims, 1 Drawing Sheet

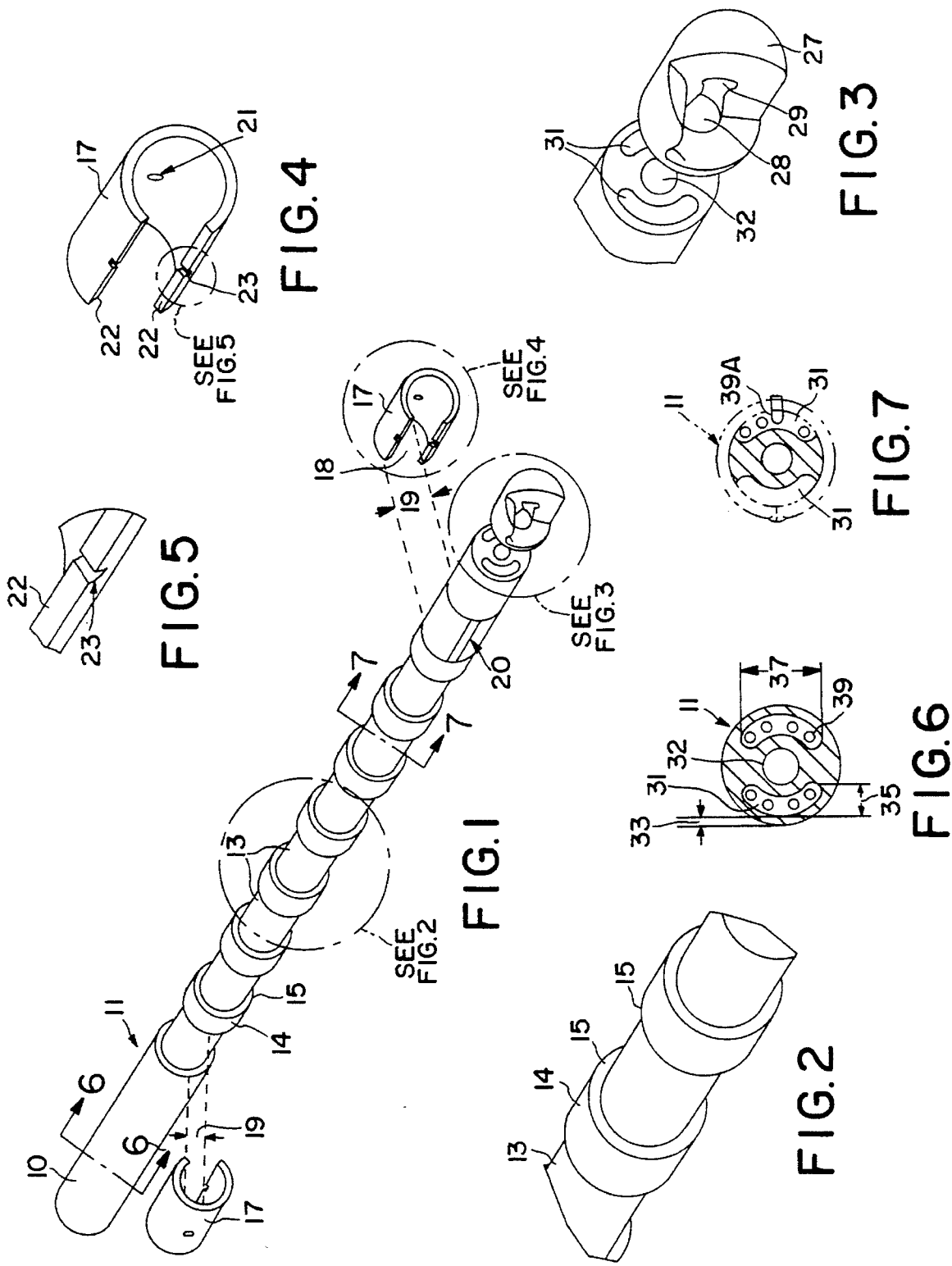

IMPLANTABLE LEAD RING ELECTRODE AND METHOD OF MAKING

BACKGROUND OF THE INVENTION

1. Field of the Invention

The present invention relates to a novel method and apparatus for providing ring electrodes of the type that are typically found at the distal portion of a body implantable lead or electrode, the function of such ring being either to provide electrical stimulation to a portion of the body or to sense spontaneous electrical signals associated with muscular movement within the body. More specifically, the invention further provides a method and a construction for a novel multielectrode stimulating or sensing lead, for example, a lead of the type that finds utility in neural stimulators.

2. Description of the Prior Art

It has long been understood that it is desirable for body implantable leads possessing ring electrodes performing a sensing or stimulating function to have an isodiametric configuration. That is, a preferred lead configuration would typically include an insulated and flexible conductor having a circular cross section that is fitted with one or more ring electrodes in such a fashion that the outer surface of the ring electrode is isodiametric with respect to the remainder of the lead. The isodiametric configuration minimizes the difficulty in passing the lead through a vein or through tissue. The smooth surface also minimizes the formation of potentially harmful thrombi when the lead is implanted. Such isodiametric construction has been achieved in different ways.

For example, Beranek, U.S. Pat. No. 4,592,372, discloses achieving an isodiametric configuration of an electrode assembly in a cardiac pacing lead by compressing a metallic sleeve which constitutes the ring electrode just far enough so that its outer diameter is the same as the outer diameter of the flexible body of the lead itself.

In Blake, et al., U.S. Pat. No. 3,995,623, there is proposed a construction for a lead useful in cardiac monitoring and temporary transvenous pacing which has multiple ring electrodes. Those ring electrodes are constructed from a coil strip of spring metal which appears to be crimped upon the electrode body with overlapping ends of the strip being joined to secure the ring electrode.

In Beranek, U.S. Pat. No. 4,608,986, a multiple lumen pacing lead having multiple ring electrodes is disclosed. Although there appears to be minimal disclosure concerning the actual method of construction of the ring electrode, it would appear from the drawings that one of the crimping techniques discussed in the above patents is used to accomplish the construction.

In Peers-Trevarton, U.S. Pat. Nos. 4,437,474 and 4,458,695 a multipolar pacing lead construction having multiple ring electrodes in an isodiametric arrangement is again disclosed. In that construction, the ring electrodes appear to be received in annular slots formed between a series of insulators which are passed over the coiled conductor of the lead and presumably cemented in place with the spaces between these insulating elements defining the slots or annular spaces for the ring electrodes.

Likewise it has been known in the prior art to build an isodiametric lead with spaced ring electrodes by cementing of gluing short sections of precut tubing onto a lead body using the appropriate adhesives and using cylindrically shaped ring electrodes that are isodiametric with the tubing as the ring electrodes. Medtronic, Inc., the assignee of this application, has offered for sale a lead for spinal cord stimulation, the Model 3487A lead, fabricated in such a manner. Conductors from within the lead body can be led through to the underside of the ring electrodes and attached to the electrodes with a laser weld. Such a construction method is labor intensive and costly.

The Model 3487A lead utilizes a coiled conductor set to traverse the lead and provide the electrical path between the ring electrodes at the distal end of the lead and the connector block which connects the lead to the stimulator device. Such coiled conductors have long been used for such applications. However, improvements in non-coiled types of conductor wire afford various benefits including improved resistance to flex fatigue, improved flexibility, and better crush resistance.

It has also been understood in the art that ring electrodes and isodiametric leads can be constructed with a multiple lumen interior with conductors from the various lumens being passed through the insulation covering the lead body to make contract with the underside of electrodes along the lead body, typically ring electrodes.

SUMMARY OF THE INVENTION

The present invention provides a method for constructing a multiple electrode isodiametric lead having multiple electrodes spaced along the lead body. Leads of such configuration find application, for example, in neural stimulation, spinal cord stimulation, and pain suppression applications. The existence of a series of ring electrodes permits the physician to optimize the effectiveness of the lead after implant by using different combinations of the spaced ring electrodes to provide stimulation. Such a lead construction also permits non-invasive reprogramming of the stimulation pattern in the event different treatment is desired or the lead is slightly dislocated as a result of the patient's physical activity. Although the particular lead configuration disclosed herein is a lead particularly adapted for neural stimulation, the principles and techniques of the instant invention can be applied to the manufacture of sensing or stimulating leads for a variety of ultimate applications.

In a second aspect, the instant invention provides for a multiple ring electrode lead, having as many as eight or more spaced ring electrodes. The lead is adapted to be used in conjunction with a stylet which can be introduced in a central lumen of the lead for purposes of stiffening it during introduction. In particular, the lead of the instant invention demonstrates superior flexibility and improved flex life properties by virtue of employing bundle strand wire conductors traversing lumens other than the stylet receiving lumen.

In accordance with the lead construction method of the instant invention, a ring electrode may be introduced onto an insulated lead in an improved fashion so as to provide an isodiametric lead construction. In the construction method, the outer layer of insulation forming the lead body is etched or notched, for example, by being laser etched or physically milled to provide a recess in the lead insulation having a depth corresponding to the thickness of the ring electrode intended to be provided at that location. A ring electrode is introduced onto the notched section on the lead in the form of a C-shaped sleeve adaptable to be introduced onto the notched portion of the lead and subsequently formable into a cylindrical shape when closed into position in said notched portion of the lead so that the edges of the C-shaped sleeve are brought to an abutting as opposed to overlapping relationship. A single conductor is brought through the insulation and aligned with a hole on the C-shaped sleeve to be welded to the sleeve, for example, by laser welding. The final affixation procedure involves laser welding the abutting surfaces of the sleeve together, thereby securely forming a ring electrode isodiametrically within the notch on the electrode. By introducing a number of such spaced C-shaped sleeves and enclosing them on multiple notches, there is provided a multiple electrode lead which by use of bundled stranded wire for the conductor possesses superior flexibility, crush resistance, and resistance against flexure fatigue. The techniques of construction, moreover, improve the efficiency of manufacture and render possible the manufacture of a multiple electrode lead having, for example, as many as eight- or more ring electrodes with significantly reduced cost.

There is also provided in accordance with this invention a neural stimulation lead having a first lumen, which may be an axial lumen, for receiving a stiffening stylet for use during lead placement and at least one other lumen containing from four to as many as eight or more bundled stranded wire conductors each of which make electrical contact with a single ring electrode on the distal portion of the lead. The lead is also characterized by isodiametric construction featuring laser welded ring electrodes emplaced in notches in the lead insulation having a depth generally corresponding to the thickness of the ring electrodes.

BRIEF DESCRIPTION OF THE DRAWINGS

FIG. 1 is an isometric view of the distal portion of a neurological lead in accordance with the instant invention showing locations for eight ring electrodes. FIG. 1 illustrates the most distal ring electrode welded in place and the most proximal ring electrode about to be assembled on the lead body.

FIG. 2 is an enlargement of a mid-section of the distal portion of the lead in FIG. 1 designated by the numeral 2 and showing in greater detail the notches formed on the lead to receive the ring electrodes.

FIG. 3 shows a detail of the lead of FIG. 1 in the area designated by the numeral 3 and illustrates the multilumen character of the main lead body as well as the configuration of a preferred tip construction for such lead.

FIG. 4 is an enlargement of the area 4 of FIG. 1 and shows in detail a ring electrode construction prior to its assembly onto the lead.

FIG. 5 shows a detail of the area 5 of FIG. 4 showing a semicircular hole which may be employed to accomplish the connection between a conductor and a ring electrode.

FIG. 6 is a cross sectional view of the body of the lead of FIG. 1 taken along line 6—6 illustrating the position of the conductors within two of the lumens of the lead and illustrating the dimension of a particular embodiment of a lead.

FIG. 7 is a cross-sectional view of the body of the lead of FIG. 1 taken along line 7—7.

DESCRIPTION OF THE PREFERRED EMBODIMENTS

The following description of the instant invention will be made in the context of the multielectrode neurological lead illustrated in the drawings. However, it will be apparent that the concepts and principles of this invention may be applied to other stimulating leads, and furthermore can be applied to the construction of ring electrodes for leads useful in other applications such as pacing leads and electrophysiologic recording leads.

FIG. 1 is an isometric view of the distal portion of a neural stimulator lead 11 with provision for eight ring electrodes. The proximate portion of the lead (not illustrated) extends proximally to the stimulator from the portion labeled 10 and terminates in a series of ring contacts which may be connected to a connector block of a type well known in the art. Such a connector block will include eight set screws adapted to engage the ring contacts at the proximal end of the lead. Each ring contact is in electrical communication with one of the ring electrodes at the distal portion of the lead thereby establishing discrete paths from the stimulator to deliver a stimulating signal to each ring electrode separately. The ring contacts may be constructed in a manner similar to that described with respect to the ring electrodes.

The distal portion of the lead is provided with eight notches 13 produced by physically milling insulation from the surface of the lead or by laser etching the insulation off the lead. Other techniques for producing the notches may be used so long as a notch of accurate and controlled dimension corresponding to the dimensions of the ring electrodes can be produced. Between the notches 13, lands 14 separate the ring electrodes, the lands 14 being formed from original insulating material as opposed to being formed of sleeves cemented in place as in the prior art. The latter type of a construction is more labor intensive to construct.

Lands 14 are raised above the notched portion of the leads by an amount 15 corresponding to the thickness of the ring electrode which, in the embodiment illustrated, is about 0.005 inch. However, different dimensions may be used depending upon the overall dimensions of the lead.

The lead body itself is made of a suitable insulating material of the type well known in the art. High quality, complex extrusions suitable for use in a multilumen lead may be created from a number of different polymers. Typically, polyurethane or silicone tubing has been most frequently used in body implantable stimulating and sensing leads. However, other thermoplastics and polymers such as nylon, polytetrafluoroethylene or the like might be adapted to such use. The particular insulating material used in construction of the lead itself is not important in the context of this invention so long as the material is a suitable biocompatible polymer that can function as an electrical insulator.

FIG. 3 shows a detail of the tip of the lead construction and also illustrates a detail of the multilumen character of the body of the lead. Central lumen 32 is axial to the lead body and is suitable for receiving a stiffening stylet to run the length of the lead 11. Two arcuate lumens 31 on opposite sides of lumen 32 can be adapted to contain conductors 39 as illustrated in FIGS. 6 and 7. Conductors 39 extend from the connector block to the individual ring electrodes at the distal end of the lead. Although the instant embodiment shows a tri-lumen lead with four conductors in each of the opposite arcuate lumens, alternative constructions could be chosen. Leads for neurological stimulation having four and as many as eight or more ring electrodes may be built. It may be desirable to arrange the stylet receiving lumen 31 in an asymmetrical position with respect to other of the lumens to obtain some advantage in steerability. In accord with this invention it is merely preferred to accommodate the conductors in a lumen other than the stylet receiving lumen because of the bundled stranded wire nature of the conductors as will be discussed more thoroughly below.

Cemented on the end of the lead body 10 is a tip 27 which is also constructed of a biocompatible plastic similar to that forming the body of the lead. Tip 27 is cemented to face 25 of the body of the lead such that blind recess 28 in the tip aligns with the stylet receiving lumen 32. In a preferred aspect of this invention, the distal interior portion of tip 27 is recessed at the most distal interior portion of the tip to receive a ball tip stylet. Such a ball shaped stylet is of the type already used in Medtronic's Model 3888 lead. The ball tip stylet (not illustrated) is advanced through lumen 32 until the ball enters tip 27. The ball may then be frictionally engaged in a recess in the tip providing increased steerability and control of the lead under certain implant circumstances.

FIG. 4 illustrates a ring electrode member prior to emplacement upon the lead. Ring electrode member 17 is provided as a C-shaped strip of electrode material, preferably platinum iridium which has an opening 19 slightly greater than the diameter of the notched portions 13 of the lead 11. After notches 13 have been milled or laser etched into the body of the lead, electrode member 17 which has a thickness corresponding to the depth of notches 13 is placed over one of the notches 13. Although electrical connection between that conductor and electrode member 17 may be accomplished in any suitable way, it is preferred to bare the end of that conductor and lead that bare conductive end through hole 21 or semicircular hole 23 on electrode member 17. It is not necessary for electrode member 17 to have both hole 21 and semicircular hole 23 inasmuch as only a single electrical connection with the electrode member 17 need be accomplished. Providing a hole in sleeve 17 provides a convenient way to mate the ring electrode with its conductor so that it can be secured by a laser weld or other fastening means.

With the conductor in contact with electrode member 17, the C-shaped member is placed over a notch 13 and is closed around notched portion 13 of the lead so that opposing surfaces 22 are in abutting relationship. In this position, the diameter of the closed and emplaced electrode member 17 corresponds to the diameter of the lands 14 which separate the ring electrodes at the distal end of the lead. Abutting edges 22 of electrode 17 are then preferably by laser welding them into place. The conductor 39 is then laser welded into hole 21 or hole 23. Those steps fully accomplish the interconnection of the ring electrode with the conductive member and accomplish an electrical path from one contact at the connector block through to the electrode member at the distal part of the lead. Other connection techniques using adhesives may be used, but as indicated above it is preferred to use a low power laser to weld the abutting edges of the electrode member 17 and to accomplish interconnection of that member with a conductor. The resulting emplacement of electrode member 17 in notch 13 creates a isodiametric construction wherein the diameter of the welded ring electrode member 17 corresponds to the outer diameter 14 of lead 11. Moreover, it will be understood that electrode member 17 is sized so as to closely fit within the notch 13 abutting the opposing surfaces 15 on the lands on opposite sides of the electrode.

Referring now to FIG. 6, there is illustrated a sectional view of lead 11 taken along line 6—6 which is in a region where the lead insulation has not been etched. The sectional view reveals the existence of two arcuate lumens 31 on opposite sides of a central stylet receiving lumen 32. In a particular embodiment of the present invention, the overall diameter of lead 11 may be suitably provided as 0.050 inch. The central lumen 32 in that embodiment has a diameter of 0.013 inch. Dimension 35 of arcuate lumen 31 is 0.007 inch while dimension 37 of the arcuate lumens is 0.030 inch. The minimum thickness of insulation 33 is 0.004 inch. Accordingly, when the laser etching or milling is accomplished it should desirably be in the neighborhood of 0.005 to 0.006 inch so as to ablate the insulation shown as dimension 33 so that arcuate lumens 31 are exposed as best illustrated in FIG. 7.

In FIG. 7 there is illustrated a sectional view of lead 11 taken along line 7—7 which is in a region where the lead insulation has been etched. As shown, the insulation has been etched to a depth sufficient to expose lumens 31 so that one of the conductors 39-A may be accessed and connected to the ring electrode which is to be affixed to the lead in this notched area.

The foregoing dimensions are provided for illustrative purposes only and are not intended to limit the scope or spirit of this invention. However, it will be understood that based upon the instant disclosure there can be provided an extremely thin isodiametric lead having a high degree of flexibility and superior flex fatigue resistance. Although in the embodiment disclosed the lead insulation has been notched or milled to accommodate the ring electrodes, it will be understood that the ring electrodes could be placed directly over the lead without notching the insulation. In that case, the ring electrodes would be compression fitted to preserve the isodiametric dimension of the lead. Alternatively, the electrodes could be fitted so that the outer surface of the electrodes is raised above the surface of the lead.

As indicated above, the superior flex and crush resistance of the lead of the instant invention is accomplished by replacing the coiled wire typically used in leads of the prior art with bundled stranded wire. Bundled stranded wire is a commercially available conductor which is a fine wire rope made of implantable conductive materials. Many different configurations of size, number and arrangements of strands are available from suitable manufacturers. For example, a suitable embodiment of bundled stranded wire preferred in the construction of this invention possesses seven individual strands, each strand having a diameter of 0.00133 inch to provide a seven-stranded bundle having an outside diameter of 0.004 inch. The bundle is twisted appropriately and provided with an insulated coating, for example, a one mil coating of polytetrafluoroethylene polymer. Such bundled stranded wire in accordance with this invention has a high degree of strength. The bundled and twisted nature of the wire provides a high degree of flex and crush resistance while maintaining flexibility and permitting the interconnection of as many as eight or more ring electrodes at the distal end of a suitable neural lead while maintaining a diameter less than approximately 0.053 inch.

There has been described herein a novel body implantable lead and a novel process for enplacing ring electrodes on body implantable leads. Use of the inventions of this application provide a relatively inexpensive lead of high quality and having improved resistance against flexure fatigue. Moreover, the instant invention facilitates the production of a neural stimulator lead having an increased number of ring electrodes at the distal end, the illustrated embodiment providing eight, thereby affording the physician greater facility to noninvasively reprogram the stimulation pattern after the lead is implanted.

While the invention herein has been described in connection with a particular embodiment, one skilled in the art will appreciate that numerous other embodiments and departures from the embodiment shown may be made without departing from the inventive concepts disclosed. For example, the lead may be used in combination with a wide range or variety of tip constructions including conductive tips, particularly if the lead is adapted to a pacing application. A wide variety of dimensions for the elements such as the ring electrodes and the lumens may be chosen. In addition other features may be added to the lead while still employing the inventive elements herein. It is therefore to be understood that, within the scope of the appended claims, the invention may be practiced in a fashion other than has been specifically described.

What is claimed is:

1. A body implantable lead comprising:

a lead body having proximal and distal ends;

at least one electrically conductive substantially annular electrode spaced along the distal end of the lead body, each of the electrodes having a discontinuity through a portion of each of the electrode members, the discontinuity forming opposed surfaces on each of the electrode members at opposite ends of the discontinuity, the opposing surfaces of the electrode members abutting and being securely fixed to one another;

a plurality of contacts spaced along the proximal end of the lead body; and a plurality of conductors each connecting one of the electrode members to a respective one of the contacts.

2. The body implantable lead of claim 1 wherein the lead body has at least a first lumen for containing the conductors.

3. The body implantable lead of claim 1 wherein the lead body has a second lumen extending coaxially with the lead body, the second lumen adapted to receive a stylet therethrough.

4. The body implantable lead of claim 1 wherein the lead body has a notch formed in the insulative material of the lead body for each electrode member and each of the electrode members are positioned in the respective notches formed in the lead body.

5. The body implantable lead of claim 4 wherein the lead body and electrode members are isodiametric.

6. The body implantable lead of claim 1 wherein each of the contacts are substantially annular and has a discontinuity through a portion of each of the contacts, the discontinuity forming opposing surfaces on each of the contacts at opposite ends of the discontinuity, the opposing surfaces of the contacts abutting and being securely fixed to one another.

7. The body implantable lead of claim 6 wherein the lead body and the contacts are isodiametric.

8. A body implantable lead comprising:

a lead body having proximal and distal ends, the lead body having a plurality of notches formed along the distal and proximal ends;

a plurality of electrically conductive substantially annular electrode members positioned within the notches formed along the distal end of the lead body, the electrode members having a discontinuity through a portion of each of the electrode members, the discontinuity forming opposed surfaces on each of the electrode members at opposite ends of the discontinuity, the opposing surfaces of the electrode members abutting and being securely fixed to one another;

a plurality of contacts positioned within the notches formed along the proximal end of the lead body, each of the contacts being substantially annular and having a discontinuity through a portion of each of the contacts, the discontinuity forming opposed surfaces on each of the contacts at opposite ends of the discontinuity, the opposing surfaces of the contacts abutting and being securely fixed to one another;

at least a first lumen located within the lead body; and a plurality of conductors located within the first lumen, each conductor connecting one of the electrode members to a respective one of the contacts.

9. The body implantable lead of claim 8 further comprising a second lumen formed in the lead body extending coaxially with the lead body, the second lumen adapted to receive a stylet therethrough.

10. A method for attaching an electrically conducting electrode to a distal end of a lead body having a distal and a proximal end, the lead body comprised of flexible insulative material, the lead body having at least one contact attached to the proximal end of the lead body, the method comprising the steps of:

fabricating a substantially annular electrically conductive electrode member having a discontinuity entirely through a portion of the electrode member so that the electrode member has the shape of a "C", the discontinuity forming opposed surfaces on the electrode member at opposite ends of the discontinuity;

placing the electrode member concentrically over the lead body at the distal end of the lead body;

closing the electrode member until the opposed surfaces of the electrode member abut to form a ring shaped electrode; and securing the opposed surfaces of the electrode member together.

11. The method of claim 10 further comprising the step of forming an electrical connection between the electrode member and the contact.

12. The method of claim 11 wherein the step of forming an electrical connection includes the steps of forming a hole in the electrode member and electrically securing a first end of an electrical conductor in the hole formed in the electrode member and electrically securing a second end of the conductor to the contact on the lead body.

13. The method of claim 12 wherein the step of forming an electrical connection includes laser welding the conductor to the hole in the electrode member.

14. The method of claim 10 further comprising the steps of forming a notch in the insulative material of the lead body to accommodate the electrode member and placing the electrode member in the notch prior to closing the electrode member and thereafter closing the electrode member until the opposed surfaces of the electrode member abut to form a ring shaped electrode member.

15. The method of claim 14 wherein the steps of forming a notch and closing the electrode member include the steps of forming the notch in the lead body and fabricating an electrode member so that when the electrode member is placed in the notch formed in the lead body and the step of closing the electrode member until the opposed surfaces of the electrode member abut to form a ring shaped electrode member is performed, the resulting ring shaped electrode member and lead body are isodiametric.

16. A method for attaching an electrically conducting electrode to a distal end of a lead body having a distal and a proximal end, the lead body comprised of flexible insulative material, the lead body having at least one contact attached to the proximal end of the lead body, the method comprising the steps of:

fabricating a substantially annular electrically conductive electrode member having a discontinuity entirely through a portion of the electrode member so that the electrode member has the shape of a "C", the discontinuity forming opposed surfaces on the electrode member at opposite ends of the discontinuity;

forming a notch in the insulative material of the lead body to accommodate the electrode member;

placing the electrode member concentrically over the lead body at the distal end of the lead body and into the notch formed in the lead body;

closing the electrode member until the opposed surfaces of the electrode member abut to form a ring shaped electrode;

wherein the steps of fabricating an electrode member and forming a notch include the steps of fabricating an electrode member and forming the notch in the lead body so that when the electrode member is placed in the notch formed in the lead body and the step of closing the electrode member until the opposed surfaces of the electrode member abut to form a ring shaped electrode member is performed, the resulting ring shaped electrode member and lead body are isodiametric;

securing the opposed surfaces of the electrode member together; and forming an electrical connection between the electrode member and the contact by forming a hole in the electrode member and laser welding a first end of an electrical conductor in the hole formed in the electrode member and electrically securing a second end of the conductor to the contact on the lead body.

17. A method of forming a ring electrode on a lead body, the lead body having distal and proximal ends and being comprised of flexible insulative material, the lead body having a conductor contained within the lead body, the method comprising the steps of:

closing a C-shaped electrically conducting member having opposing surfaces over the lead body until the opposing surfaces abut to form a ring electrode;

securing the opposing surfaces together when closed over the lead body;

establishing an electrical connection between the ring electrode and the conductor contained within the lead body by forming a hole in the C-shaped member for receiving an end of the conductor contained within the lead body.

18. The method of claim 17 wherein the step of establishing an electrical connection includes laser welding the conductor to the hole in the C-shaped member.

* * * * *